(12) United States Patent
Buck et al.

(10) Patent No.: US 8,237,715 B2
(45) Date of Patent: Aug. 7, 2012

(54) METHOD AND SYSTEM FOR MANIPULATING GROUPS OF DATA REPRESENTATIONS OF A GRAPHICAL DISPLAY

(75) Inventors: Schuyler Buck, Muncie, IN (US); Jason Bush, Fishers, IN (US); Alan Greenburg, Indianapolis, IN (US); David Bradley Markisohn, Indianapolis, IN (US); Leon R. Organ, III, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 784 days.

(21) Appl. No.: 12/205,582

(22) Filed: Sep. 5, 2008

(65) Prior Publication Data

US 2010/0064243 A1 Mar. 11, 2010

(51) Int. Cl.
*G06T 11/20* (2006.01)

(52) U.S. Cl. ............... 345/440; 345/619; 345/440.2; 715/771; 604/151

(58) Field of Classification Search .......... 345/440, 345/440.2
See application file for complete search history.

(56) References Cited

U.S. PATENT DOCUMENTS

| | | | |
|---|---|---|---|
| 2002/0080150 A1* | 6/2002 | Nakatani | 345/660 |
| 2003/0114836 A1 | 6/2003 | Estes et al. | |
| 2003/0163223 A1 | 8/2003 | Blomquist | |
| 2004/0077997 A1 | 4/2004 | Jasperson et al. | |
| 2007/0016449 A1 | 1/2007 | Cohen et al. | |
| 2007/0033074 A1 | 2/2007 | Nitzan et al. | |
| 2007/0066956 A1 | 3/2007 | Finkel | |
| 2007/0106135 A1 | 5/2007 | Sloan et al. | |
| 2007/0112298 A1 | 5/2007 | Mueller, Jr. et al. | |
| 2008/0034323 A1 | 2/2008 | Blomquist | |

FOREIGN PATENT DOCUMENTS

| | | | |
|---|---|---|---|
| WO | WO2007/000427 A1 | 1/2007 | |
| WO | WO2008/048582 A1 | 4/2008 | |

OTHER PUBLICATIONS

Simon, Jinjer. "Excel 2000 in a Nutshell", O'Reilly Media, Inc, Aug. 2000, pp. 235-261.*
Excel 2003 screen shots.*
Disetronic, "DiagLog Pump Programming Tool," Reference Manual, ver. 02 (Jun. 2005).
Medtronic Minimed, "Solutions Pumps and Meters Software," Manual, ver7.0 (2005).
Disetronic Medical Systems AG, "Accu-Chek Insulin Pump Configuration Software," User Manual, (2005).
Animans Corporation, "ezManager PLUS," User Manual, (2007).
International Search Report on Patentability for PCT/EP2009/061430 issued by the European Patent Office on Apr. 9, 2009 (4 pages).

* cited by examiner

*Primary Examiner* — Michelle L Sams
(74) *Attorney, Agent, or Firm* — Faegre Baker Daniels LLP

(57) ABSTRACT

A system is disclosed wherein a graphical representation of a profile may be adjusted to adjust one or more values of the profile. The profile may includes data values corresponding to respective time periods. The data values being represented by data representations in the graphical representation. A non-contiguous grouping of the data representations may be selected by an operator to adjust the data values of the profile corresponding to the non-contiguous grouping of data representations. A contiguous grouping of the data representations may be selected by an operator to adjust the data values of the profile corresponding to the non-contiguous grouping of data representations.

30 Claims, 13 Drawing Sheets

METHOD AND SYSTEM FOR MANIPULATING GROUPS OF DATA REPRESENTATIONS OF A GRAPHICAL DISPLAY

FIELD OF THE INVENTION

The present teachings generally relate to the manipulation of graphical representations of data and in particular to the manipulation of a data profile through a manipulation of a graphical representation of the data profile.

BACKGROUND

An insulin pump is a fluid infusion device for delivering insulin to people who suffer from diabetes. The insulin pump, which is worn by the user and eliminates the need for multiple daily insulin injections, closely imitates a normally functioning pancreas by releasing hundreds of small doses of insulin each day into the body through an infusion set to regulate blood glucose levels. The rate of delivery of these small doses (i.e., the basal rate) varies from user to user. Indeed, even for a particular user, the basal rate varies throughout the day, and depends upon a variety of factors such as the user's internal clock, metabolism, physical health, and level of stress and exercise. A basal rate profile may divide a day into 24 hourly basal periods each having an associated basal rate. It should be understood that although portions of this description refer to hourly basal rates and basal rate profiles, basal rates may cover more or less than a one hour time period. Indeed, the time periods covered by basal rates in a profile need not be equal. The concepts of the present disclosure are not limited by the duration of an individual basal rate, and the references to hourly basal rates are only exemplary.

Many users use different basal rate profiles for different circumstances. For example, one basal rate profile may be used for weekdays, another profile (i.e., with different hourly basal rates) for weekends, and another profile for vacation days. These different basal rate profiles are designed to accommodate the expected differences in the user's background insulin needs resulting from variations in the user's sleep patterns, levels of exercise and stress, health condition, menstruation cycle status, etc. during such periods.

As the amount and rate of insulin delivery must be tailored to the individual needs of the user, modern pumps are programmable. Some pumps are capable of communicating with a separate computing device, and are compatible with programming software applications that may be executed on the computing device. The programming software permits an operator, such as the user or a health care provider, to customize the settings of the various parameters that affect the pump's operation. These parameters are included in a configuration file that is executed by the pump, and include hourly basal rates, maximum hourly basal rates, bolus dose settings, communication settings, battery settings, and many others.

As suggested by the foregoing, insulin pumps perform relatively complex functions, which directly affect the health of the user. For at least these reasons, configuration software is generally designed to simplify, to the extent possible, the processes for programming pump functions. It is desirable to provide flexibility to the operator in programming the basal rate profiles such that various operator selected groups of basal rates may changed.

SUMMARY

The present disclosure provides software to manipulate graphical representations of data. The present disclosure also provides software to manipulate a data profile through a manipulation of a graphical representation of the data profile.

In an exemplary embodiment of the present disclosure, there is provided a method for adjusting data values. The method includes the step of displaying a plurality of data representations in a graphical format. Each data representation corresponds to a data value of a profile. The method further includes the step of receiving a selection of a first portion of the plurality of data representations. The first portion of the plurality of data representations includes a non-contiguous group of the plurality of data representations. The method further includes the steps of receiving at least one input to simultaneously adjust the data representations of the first portion of the plurality of data representations, and adjusting the data values of the profile corresponding to the data representations of the first portion of the plurality of data representations based on the received at least one input. In an example thereof, the step of receiving the at least one input to simultaneously adjust the data representations of the first portion of the plurality of data representations includes the step of altering the plurality of data representations of the first portion to represent one of a reduction in the corresponding data values of the profile by a first offset and an increase in the corresponding data values of the profile by a second offset. In a variation thereof, the plurality of data representations are bar segments of a bar graph and the step of altering the plurality of data representations of the first portion to represent one of a reduction in the corresponding data values of the profile by a first offset and an increase in the corresponding data values of the profile by a second offset includes the step of with a pointer device simultaneously dragging a current height of each the bar segments of the first portion to an adjusted height corresponding to one of the first offset from the current height and the second offset from the current height. In another variation thereof, the plurality of data representations are bar segments of a bar graph and the step of altering the plurality of data representations of the first portion to represent one of a reduction in the corresponding data values of the profile by a first offset and an increase in the corresponding data values of the profile by a second offset includes the step of with a keyboard simultaneously moving a current height of each the bar segments of the first portion to an adjusted height corresponding to one of the first offset from the current height and the second offset from the current height, a first key of the keyboard being used to move the current height of each of the bar segments of the first portion to the adjusted height corresponding to the first offset and a second key of the keyboard being used to move the current height of each of the bar segments of the first portion to the adjusted height corresponding to the second offset.

In another exemplary embodiment of the present disclosure, a method of adjusting insulin basal rates for an insulin pump is provided. The method includes the steps of receiving a plurality of insulin basal profiles from the insulin pump, storing the plurality of insulin basal profiles, displaying a graphical representation of each of the plurality of insulin basal profiles, and receiving a selection of a first insulin basal profile of the plurality of insulin basal profiles. Each of the plurality of insulin basal profiles providing insulin basal rates for a plurality of time periods of a twenty-four hour period. The method further includes the step of displaying a second graphical representation of the first insulin basal profile. The second graphical representation includes a first axis indicating a time scale, a second axis indicating an insulin basal rate scale, and a plurality of data representations. Each data representation corresponds to a time period of the plurality of time periods and providing an indication of a corresponding insulin basal rate for the time period. The method further includes the steps of receiving a selection of a first non-contiguous grouping of data representations corresponding to a first non-contiguous grouping of time periods of the first insulin basal rate profile, simultaneously adjusting the first non-contiguous grouping of data representations to adjust an indication of the corresponding insulin basal rate for each of the time periods of the first non-contiguous grouping of time periods, and storing an adjusted first insulin basal rate profile. The adjusted first insulin basal rate profile includes adjusted insulin basal rates for the first non-contiguous grouping of time periods. The adjusted insulin basal rates is based on the adjusted first non-contiguous grouping of data representations. The method further includes the step of communicating the adjusted first insulin basal rate profile to the insulin pump. In an example thereof, the plurality of data representations are bar segments and the indication of the corresponding insulin basal rate for each of the plurality of data representations includes a height of the corresponding bar segment. In a variation thereof, the step of receiving the selection of the first non-contiguous grouping of data representations corresponding to the first non-contiguous grouping of time periods of the first insulin basal rate profile includes the steps of receiving a first input selecting a first bar segment of the bar segments of the first non-contiguous grouping of data representations, and receiving a second input selecting a second bar segment of the bar segments of the first non-contiguous grouping of data representations. Further, the step of simultaneously adjusting the first non-contiguous grouping of time periods includes the steps of receiving a third input corresponding to adjusting a height of the first non-contiguous grouping of data representations including a first adjusted height corresponding to the first bar segment and a second adjusted height corresponding to the second bar segment; and displaying the plurality of bar segments corresponding to the first non-contiguous grouping of data representations, the first bar segment being displayed with the first adjusted height and the second bar segment being displayed with the second adjusted height. In a further variation thereof, the step of receiving the selection of the first non-contiguous grouping of data representations corresponding to the first non-contiguous grouping of time periods of the first insulin basal rate profile further includes the step of receiving a fourth input selecting a group type as a non-contiguous group, the fourth input being received prior to the second input. In another variation, the third input corresponds to a fixed offset. In yet another variation, the third input corresponds to a percentage offset. In another example thereof, the method further includes the step of displaying a representation of an original first height of the first bar segment along with the first adjusted height of the first bar segment and an original second height of the second bar segment along with the second adjusted height of the second bar segment.

In a further exemplary embodiment of the present disclosure, a method for adjusting data values is provided. The method includes the steps of displaying a plurality of data representations in a graphical format, each data representation corresponding to a data value of a profile, receiving a first input corresponding to a selection of a first data representation and a second input, the second input corresponding to one of a contiguous group selection and a non-contiguous group selection, receiving a third input corresponding to a selection of a second data representation, defining a contiguous group of data values of the profile corresponding to data representations bounded by the first data representation and the second data representation when the second input corresponds to the contiguous group selection, defining a non-contiguous group of data values of the profile corresponding to data representations including the first data representation and the second data representation when the second input corresponds to the non-contiguous group selection, and simultaneously adjusting each of the defined group of data values in response to a received adjustment input. In an example thereof, the profile is a basal rate profile for an insulin pump and the plurality of data values are a plurality of basal rates of insulin to be administered by the insulin pump. In a variation thereof, the plurality of data representations are a plurality of bar segments corresponding to the plurality of basal rates of insulin to be administered by the insulin pump. In another variation thereof, the method further includes the steps of storing an adjusted basal rate profile including each of the data values of the defined group; and communicating the adjusted basal rate profile to the insulin pump. In another example thereof, the first input and the third input is received from a pointer device and the second input is received from a keyboard. In a variation thereof, the second input corresponding to a contiguous group selection is based on a shift key of the keyboard and the second input corresponding to a non-contiguous group selection is based on a control key of the keyboard. In yet another example, the simultaneously adjusting step includes the step of receiving inputs from a pointer device resulting from a user clicking on a data representation corresponding to one of the data values in the defined group of data values and altering a position of the data representation. In a variation thereof, the simultaneously adjusting step includes the step of changing each of the data values in the defined group by an offset, the offset corresponding to the position of the data representation. In a further example, the simultaneously adjusting step includes the steps of setting each of the data values in the defined group to an equal value and changing each of the data values in the defined group by a fixed amount. In another example, the method further includes the step of displaying adjusted data representations corresponding to the defined group as a real time visual feedback. In still another example, the method further includes the step of displaying an adjustment field, wherein the simultaneously adjusting step includes the step of receiving an input from a keyboard resulting from a user entering a value in the adjustment field. In a variation thereof, the simultaneously adjusting step includes the step of setting each of the data values in the defined group to the entered value.

In yet another exemplary embodiment of the present disclosure, an apparatus for adjusting insulin basal rates for an insulin pump is provided. The apparatus includes a computing device, a memory accessible by the computing device, a display operatively coupled to the computing device, at least one user input device operatively coupled to the computing device, and software stored on the memory which provides a user interface to display a graphical representation of a first insulin basal profile for the insulin pump including a data representation for a plurality of time periods of the first insulin basal profile and corresponding insulin basal rates for each of the plurality of time periods. The software includes means for selecting a non-contiguous group of data representations of a first portion of the plurality of time periods for adjustment and means for simultaneously adjusting the corresponding insulin basal rates for each of the data representations of the first portion of the plurality of time periods. In an example, the software further includes means for selecting a contiguous group of data representations of a second portion of the plurality of time periods for adjustment. In another example, the means for simultaneously adjusting the corresponding insulin basal rates for each of the data representations of the first portion of the plurality of time periods includes means for adjusting the corresponding basal rates for each of the data representations of the first portion of the plurality of time periods by a fixed offset. In yet another example, the means for simultaneously adjusting the corresponding insulin basal rates for each of the data representations of the first portion of the plurality of time periods includes means for adjusting the corresponding basal rates for each of the data representations of the first portion of the plurality of time periods by a percentage.

In still a further exemplary embodiment of the present disclosure, a computer readable medium is provided. The computer readable medium tangibly embodying instructions executable by a computing device to perform method steps including displaying a graphical representation of a current basal rate profile. The basal rate profile having a plurality of time periods and associated basal rates. The graphical representation includes a plurality of data representations corresponding to the plurality of time periods and associated basal rates of the basal rate profile. The method steps further include permitting the selection of a non-contiguous group of the plurality of data representations and simultaneously adjusting a characteristic of the non-contiguous group of the plurality of data representations to represent an adjusted basal rate for each of the time periods of the non-contiguous group of the plurality of data representations. In an example thereof, the computer readable medium further includes instructions to display the current basal rate profile and the adjusted basal rate profile simultaneously.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

It should be understood that although the concepts below are described as relating to insulin pump configuration software, such as the ACCU-CHEK® Insulin Pump Configuration Software provided by Roche Diagnostics Corporation, the concepts may also relate to diabetes management software systems for tracking and analyzing health data, such as, for example, the ACCU-CHEK® 360° product provided by Roche Diagnostics Corporation. Moreover, the concepts described herein may also have applicability to apparatuses, methods, systems, and software in fields that are unrelated to healthcare. Furthermore, it should be understood that references in this patent application to devices, pumps, meters, monitors, or related items are intended to encompass any currently existing or later developed apparatus that includes some or all of the features attributed to the referred to apparatus, including but not limited to the ACCU-CHEK® Active, ACCU-CHEK® Aviva, ACCU-CHEK® Compact, ACCU-CHEK® Compact Plus, ACCU-CHEK® Integra, ACCU-CHEK® Go, ACCU-CHEK® Performa, ACCU-CHEK® Spirit, ACCU-CHEK® D-Tron Plus, and ACCU-CHEK® Voicemate Plus, all provided by Roche Diagnostics Corporation or divisions thereof.

Figure 1:
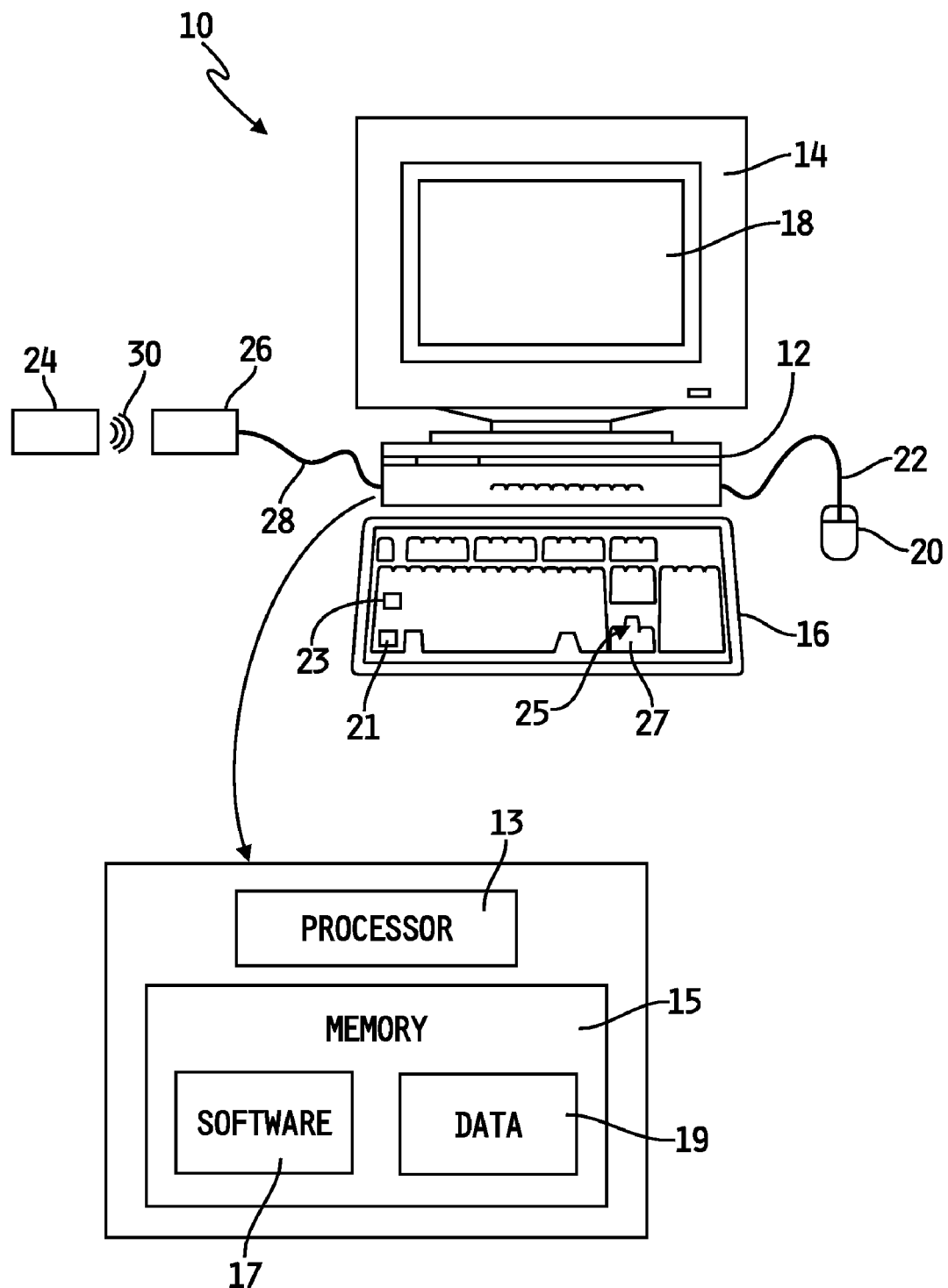
FIG. 1 is a conceptual diagram of a computing device in communication with an insulin pump.

Turning now to the figures, FIG. 1 depicts an exemplary embodiment of a system 10, some or all of the components of which may be used in conjunction with the teachings of the present disclosure. System 10 generally includes a computing device 12, shown here in the form of a computer having display device 14, in this case a computer video screen or monitor having screen 18, a keyboard 16, a processor 13, and memory 15, which may contain the software 17 of the present disclosure and data 19 as is further described herein. Keyboard 16 includes control key 21 and shift key 23. While described and depicted herein with specific reference to a computer, certain concepts of the present disclosure may be utilized in conjunction with any computing device capable of operating pump programming software. Computing device 12 also has a mouse or pointer device 20 connected to it by cable 22 (or wirelessly). While pointer device 20 and keyboard 16 are shown, system 10 may include any input device such as a touchpad, joystick, touch screen, trackball, etc.

Computing device 12 may include a variety of computer-readable media. Computer-readable media can be any available media that can be accessed by computing device 12 and includes both volatile and non-volatile media, and removable and non-removable media. By way of example, and not limitation, computer-readable media may comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules and other data and which can be accessed by computing device 12. Computer-readable media may be accessed directly or through a network such as the Internet.

System 10 is configured to provide information to, and receive information from, infusion pump 24. Again, while an infusion pump, and more particularly an insulin pump, is described herein, it should be understood that the teachings of the present disclosure may also apply to devices such as "smart" insulin pens or other such devices known or hereafter developed. In FIG. 1, computing device 12 is shown coupled to communication media or dongle 26, in this case a modulated signal transceiver, accessible to computing device 12 by means of cable 28, and configured to transmit and receive modulated signal 30 to establish logical communication with pump 24. In another exemplary embodiment, computing device 12 and pump 24 may include ports configured to establish a physical connection. By way of example, and not limitation, dongle 26 may include wired media such as a wired network or direct wired connection, and wireless media such as acoustic, RF, infrared and other wireless media. More specifically, dongle 26 as depicted includes an infrared port for communication with a similar infrared port of pump 24.

Figure 2:
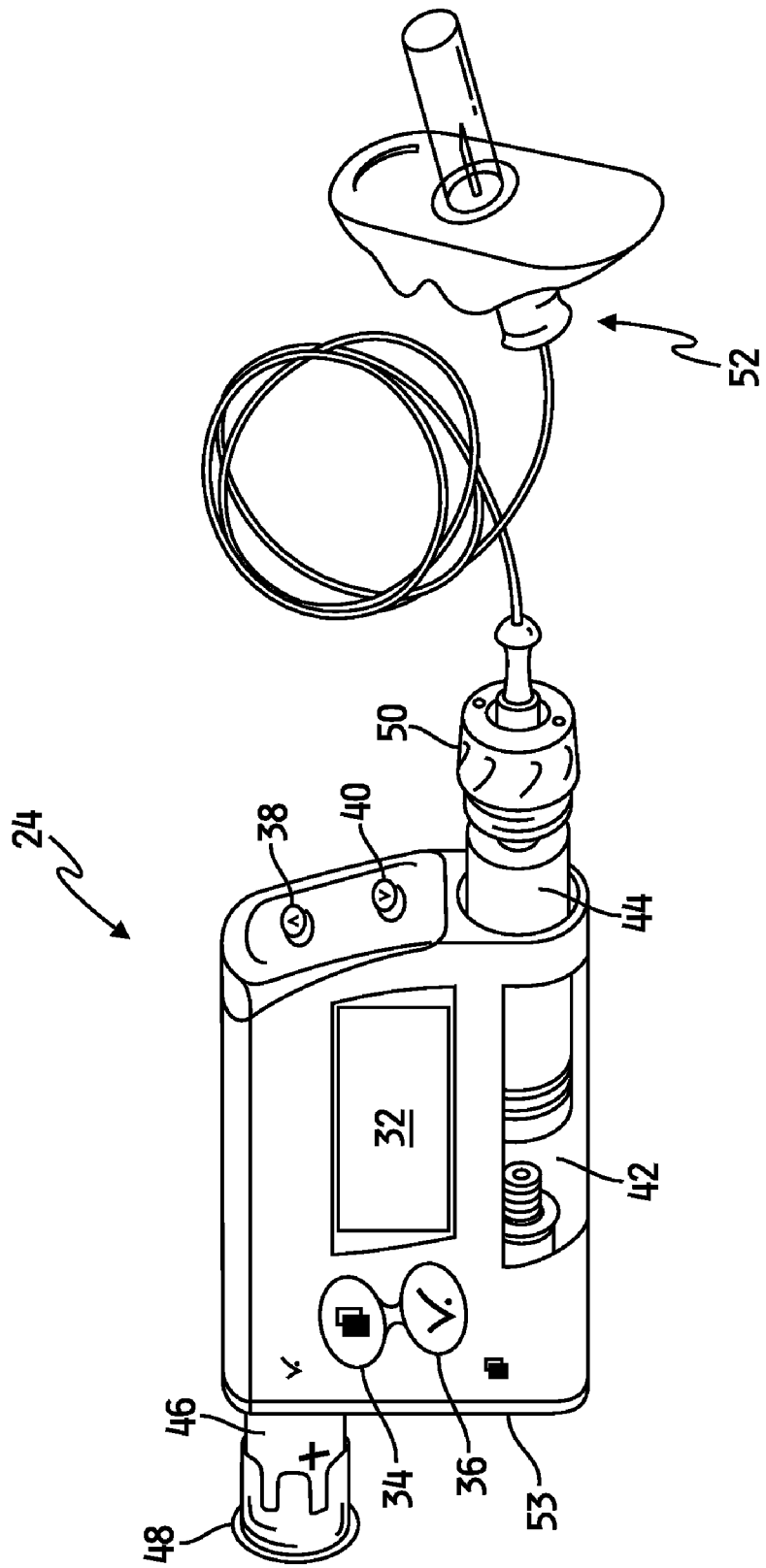
FIG. 2 is perspective view of an insulin pump coupled to an infusion set.

Referring now to FIG. 2, pump 24 includes a display 32 for displaying information to an operator or user, a menu button 34 for navigating though the various functions provided by pump 24, a check button 36 for selecting options, an up key 38 and down key 40 for scrolling through options and controlling certain insulin delivery functions, a cartridge receptacle 42 for storing an insulin cartridge 44, a battery 46 (shown partially inserted), a battery cap 48 (shown unsecured to pump 24), an adapter 50 for physically coupling cartridge 44 to an infusion set 52, and a communication port 53 for sending information to, or receiving information from, computing device 12 through dongle 26.

Figure 3:
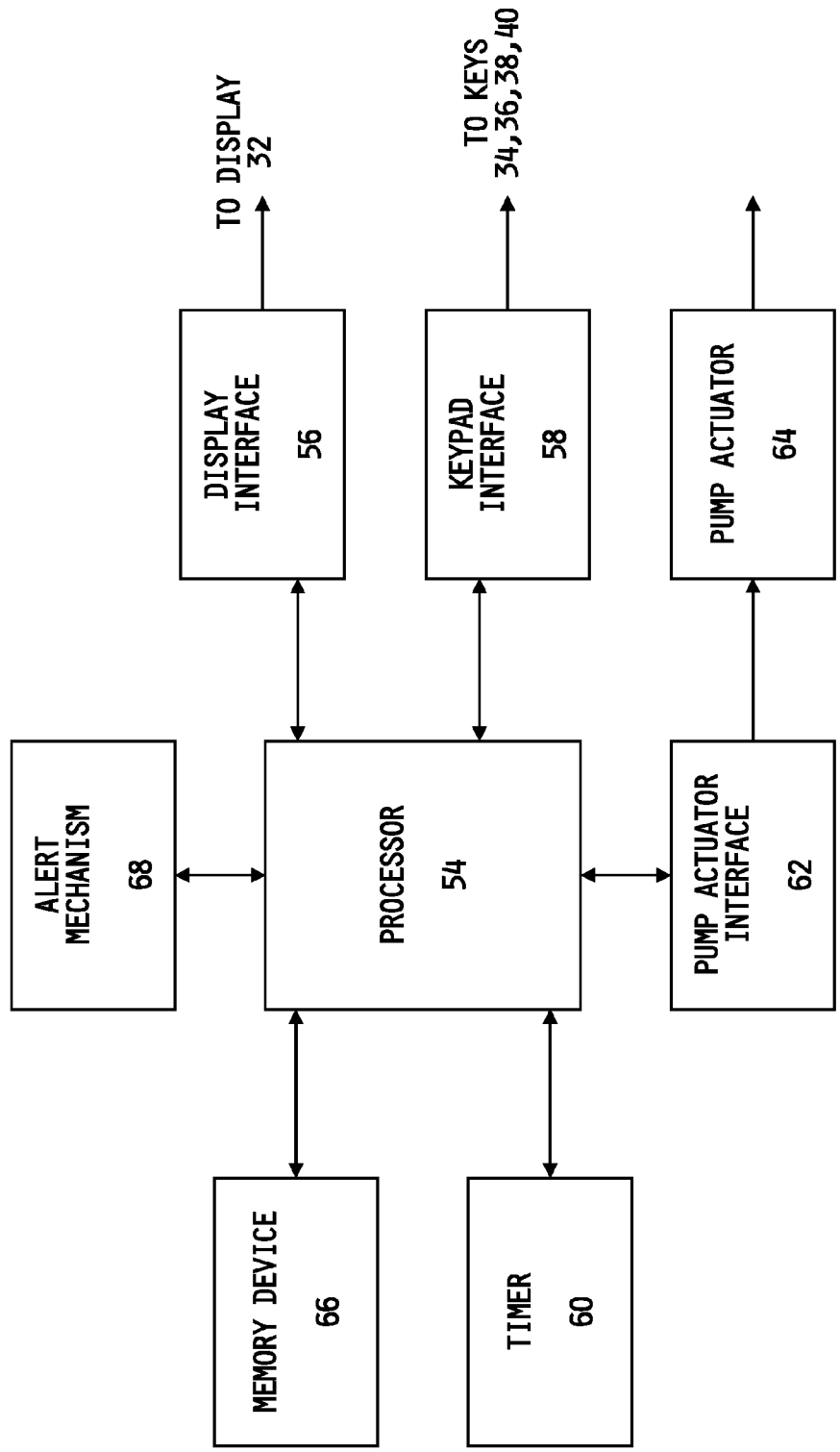
FIG. 3 is a block diagram of internal components of the pump of FIG. 2.

FIG. 3 provides a block diagram representation of internal components of pump 24. As shown, pump 24 includes a processor 54 coupled to a display interface 56, which is coupled to display 32. Processor 54 is also coupled to a keypad interface 58 which is coupled to keys 34, 36, 38, 40, and a pump actuator interface 62 which is coupled to an actuator 64 suitable for delivering insulin doses (medical infusion pumps other than insulin pumps will deliver doses of other medicament). Processor 54 is further coupled to a memory device 66 that stores application programs and data, including the configuration files described herein. Memory device 66 is constructed of any combination of volatile and/or nonvolatile memory suitable for a particular embodiment. Processor 54 is also coupled to an alert mechanism 68, that, in various embodiments is a buzzer, a vibrator, a light emitting diode, or the like, suitable for providing audible, tactile, or visual alerts to an insulin pump user. Finally, processor 54 is coupled to a timer 60, which is capable of maintaining a current time, including time of day and day of the week.

Figure 4:
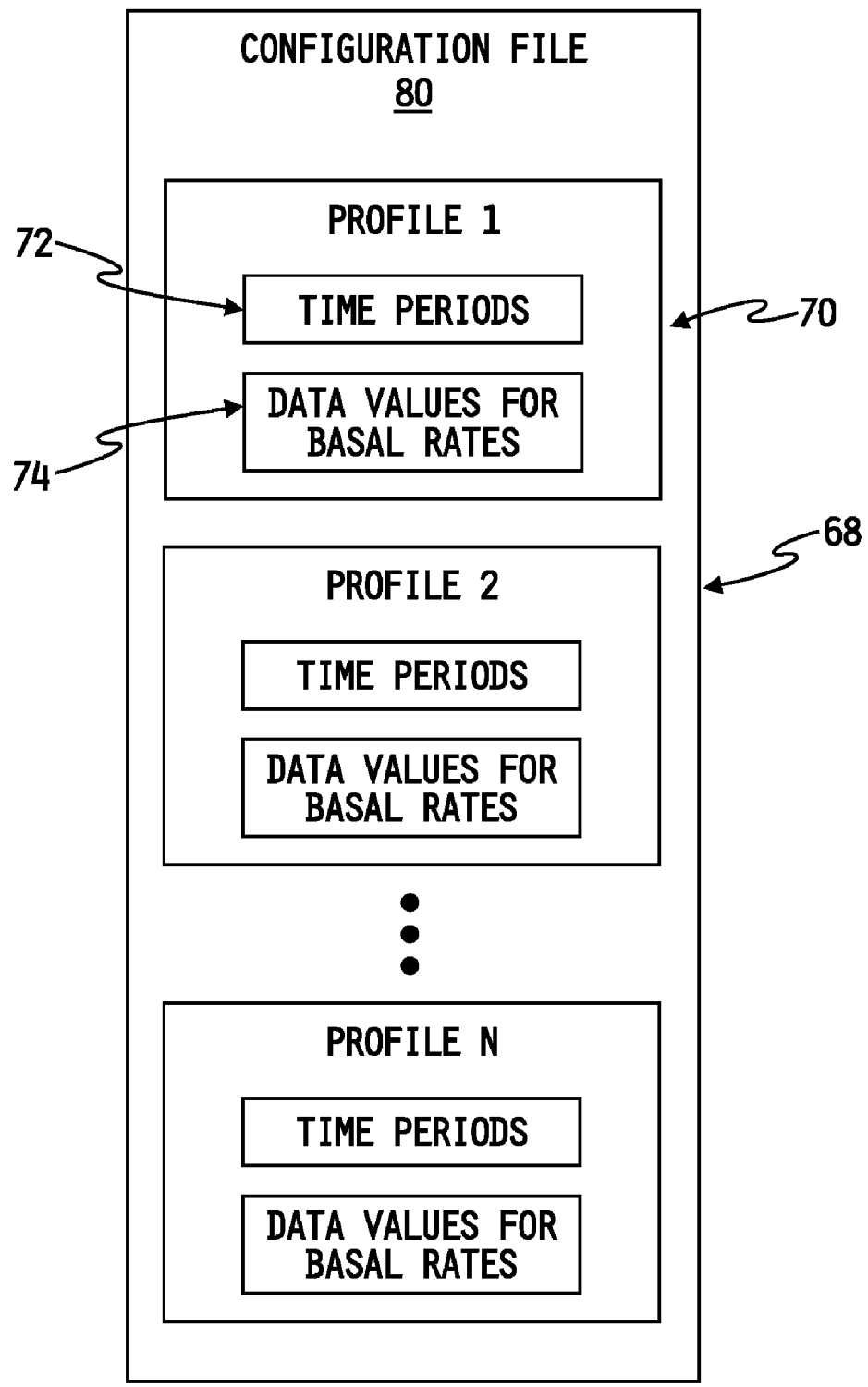
FIG. 4 is a representation of a configuration file.

For the purpose of the illustrative example of the operation of software 17, assume the operator is a health care provider who wishes to change the hourly basal rates of a basal rate profile for a user of insulin pump 24. As will be described below, in this example scenario, the operator will read a configuration file 80 (see FIG. 4) from insulin pump 24 or from memory 15 and change a basal rate profile 70 for the user associated with insulin pump 24. Configuration file 80 includes a plurality of basal rate profiles 68 including basal rate profile 70. In one embodiment, basal rate profile 70 includes a plurality of time periods 72 each having a data value, in particular a specified basal rate 74 for that time period. In one example, the plurality of time periods are one hour increments which define a twenty-four hour day and the specified basal rate 74 for each hour is a constant rate. In one embodiment, the basal rate profile 70 is provided as a part of a configuration file 80 which is stored on insulin pump 24.

Figure 5:
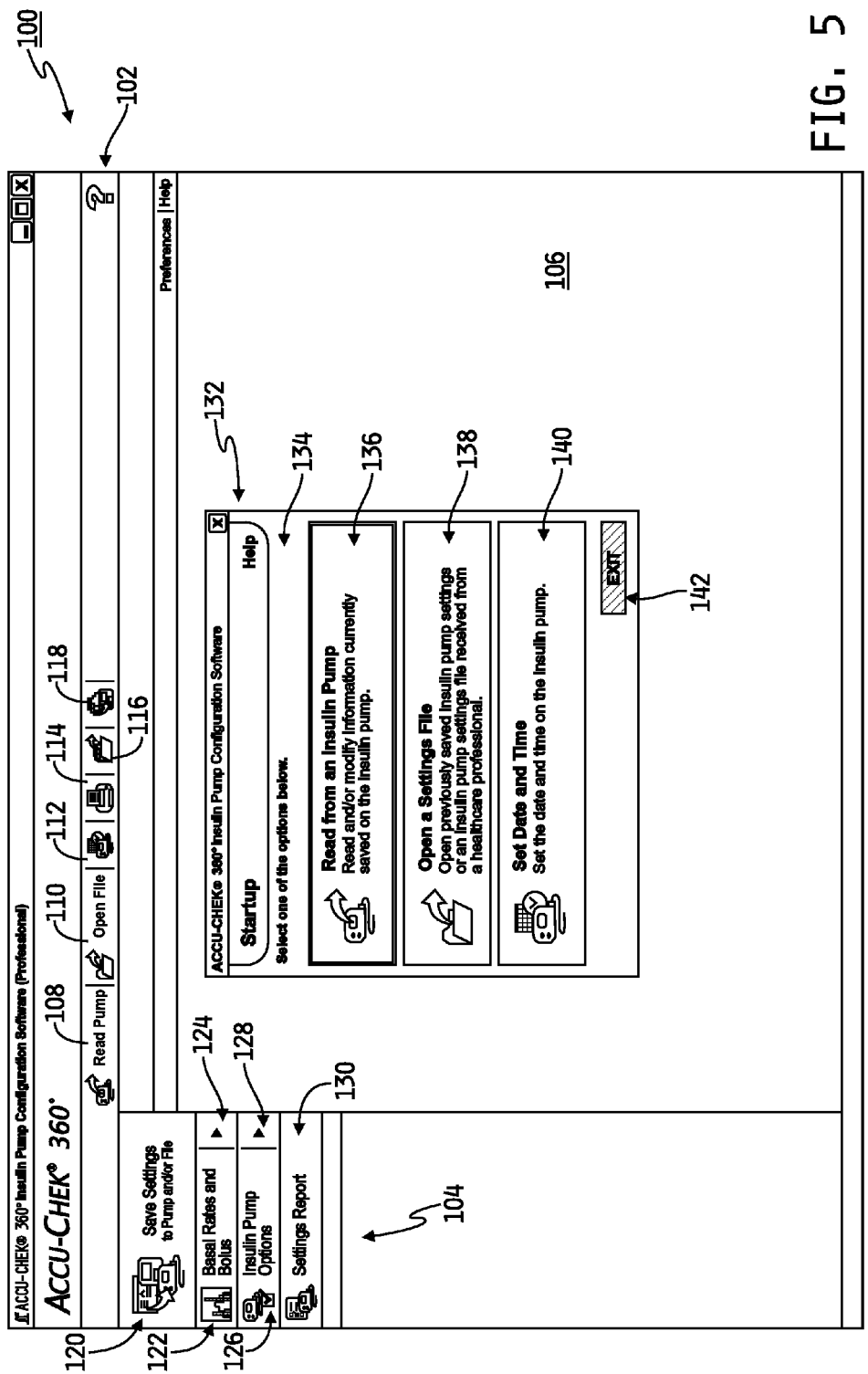
FIG. 5 is a screenshot of a home screen displayed upon activation of software according to teachings of the present disclosure.

FIG. 5 depicts a home screen 100 displayed upon activation of software 17. Home screen 100 generally includes a toolbar 102, a navigation menu 104, and an active window 106. Toolbar 102 includes a read pump icon 108, an open file icon 110, a date/time icon 112, a print icon 114, a load all profiles from file icon 116, and a save all profiles to a file icon 118. Navigation menu 104 includes a save settings button 120, a basal rates and bolus button 122 with indicator 124 that indicates the existence of a dropdown menu associated with basal rates and bolus button 122, an insulin pump options button 126 with a similar indicator 128, and a setting report button 130. The content of active window 106 changes depending upon the operation being performed by software 17. Here, active window 106 include a start up dialog box 132.

Start up dialog box 132 includes a message area 134, a read pump button 136, an open file button 138, a set date/time button 140, and an exit button 142. The operator may obtain an insulin pump configuration file 80 from insulin pump 24 using read pump button 136. Further, the operator may save a configuration file 80 to insulin pump 24 or to memory 15 associated with computing device 12. The process for obtaining or retrieving a configuration file 80 from either insulin pump 24 or a memory 15 associated with computing device 12 and for saving a configuration file 80 to either insulin pump 24 or a memory 15 associated with computing device 12 is further disclosed in co-pending patent application entitled "INSULIN PUMP PROGRAMMING SOFTWARE FOR SELECTIVELY MODIFYING CONFIGURATION DATA," U.S. Ser. No. 12/205,600, and co-pending patent application entitled "INSULIN PUMP CONFIGURATION PROGRAMMING INVALID SETTINGS NOTIFICATION AND CORRECTION," (hereinafter, "the Invalid Settings Application"), U.S. Ser. No. 12/205,587, the entire disclosures of which are hereby expressly incorporated herein by reference.

Figure 6:
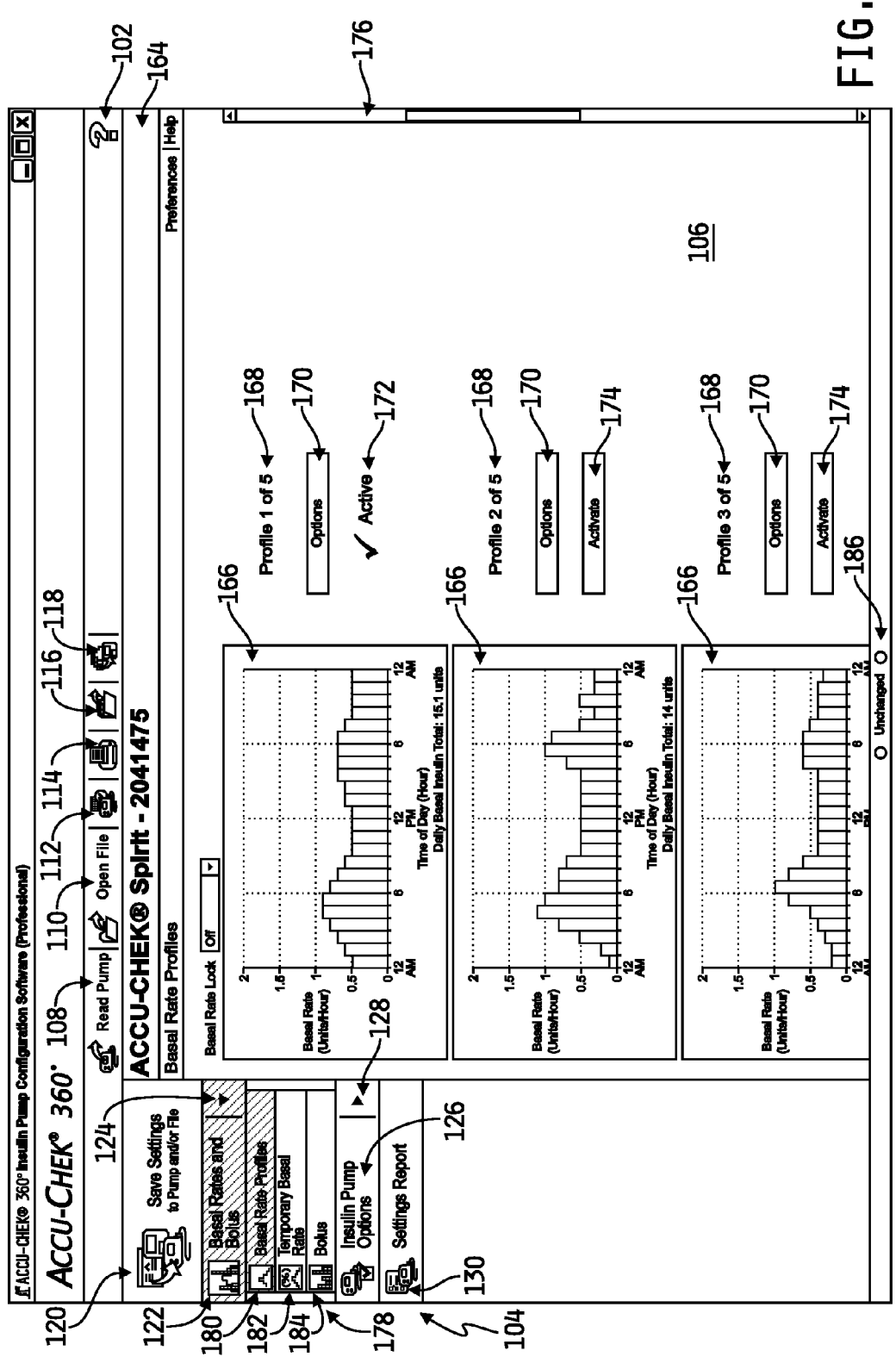
FIG. 6 is a screenshot of a display generated upon activating a configuration file.

Once the configuration file 80 is read by software 17, the operator is provided information in active window 106 regarding the plurality of basal rate profiles 68 included in the configuration file 80 as depicted in FIG. 6. In the depicted context, active window 106 includes a title bar 164 that identifies insulin pump 24 by name and serial number, at least one basal profile thumbnail image 166 that functions as a graphic preview of the data associated with a specific basal rate profile 70 included in the configuration file 80, at least one profile designation 168 indicating the number of the corresponding basal rate profile 70 represented by the associated thumbnail image 166, at least one options button 170, and an active icon 172 and/or an activate button 174. The preview function of thumbnail images is further described in co-pending patent application entitled "INSULIN PUMP PROGRAMMING SOFTWARE WITH BASAL PROFILE PREVIEW FEATURE," U.S. Ser. No. 12/205,570, the entire contents of which is hereby incorporated herein by reference.

In one embodiment, the configuration file 80 includes a plurality of basal rate profiles 68. In one example, five basal rate profiles are included in configuration file 80. Accordingly, a basal profile thumbnail image 166, profile designation 168, options button 170, and an active icon 172 and/or an activate button 174 is displayed for each of the five basal rate profiles (three basal rate profiles are represented in the FIG. 6). The operator may view basal rate profile information not shown in active window 106 by using scroll bar 176. By default, the first depicted basal rate profile is designated as active by software 17. As such, active icon 172 is shown in association with basal profile thumbnail image 166 instead of activate button 174. The operator may select other available basal rate profiles to be made active by selecting the activate button 174 associated with the desired basal rate profile.

As is also shown in FIG. 6, when a configuration file 80 is read or opened and active window 106 is populated with basal rate profile information, a dropdown menu 178 is displayed in navigation menu 104. Dropdown menu 178 includes a basal rate profile button 180 (which is depicted as active), a temporary basal rate button 182, and a bolus button 184. In the example that follows, basal rate profile information will be modified to illustrate the principles of the present disclosure for manipulating graphical representational to adjust the data values associated with a profile. Finally, active window 106 further includes a status bar 186 which indicates the status of the currently active configuration file. Here, the status is unchanged.

Figure 7:
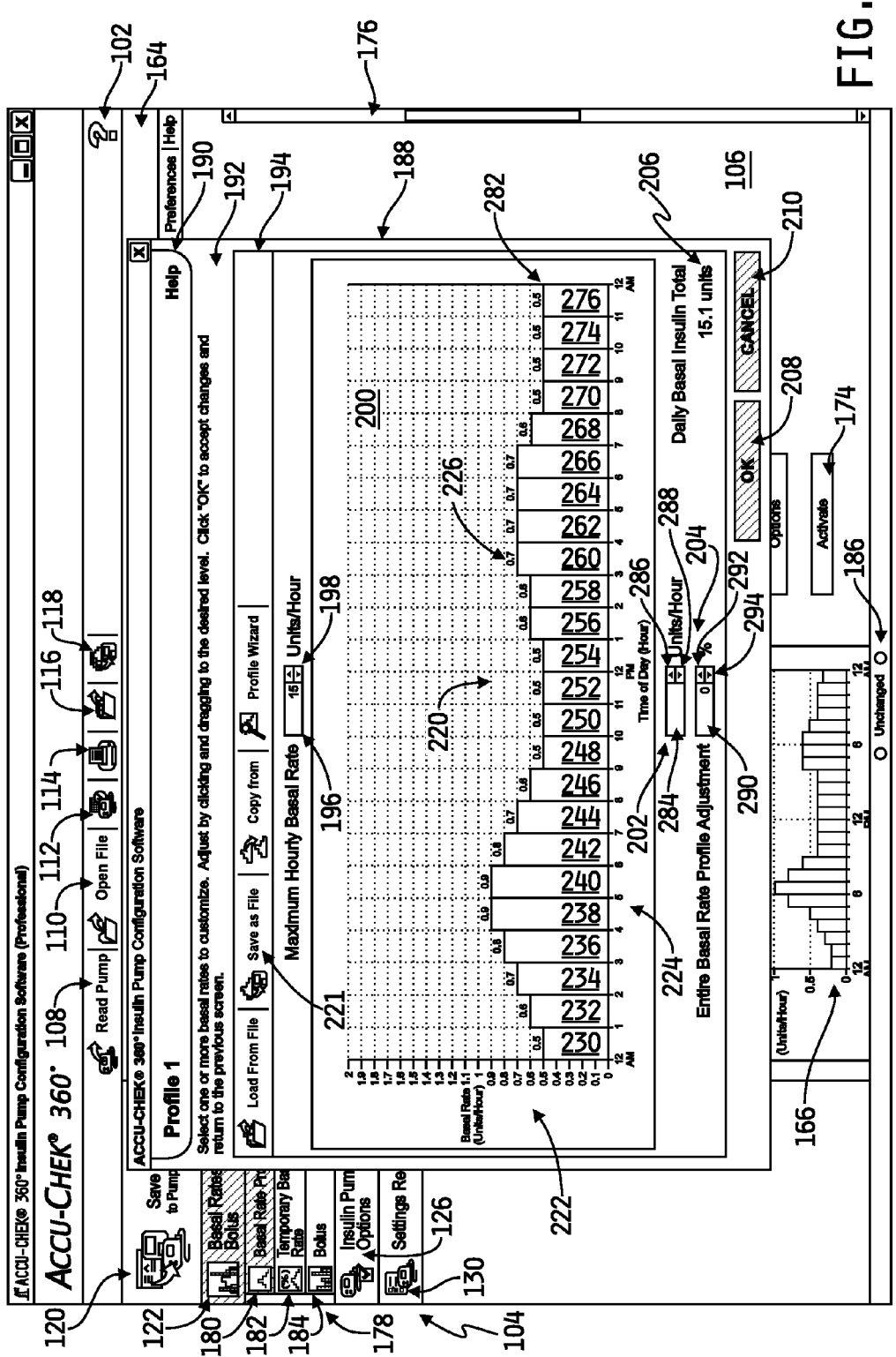
FIG. 7 is a screenshot of a display depicting a profile edit window generated upon selecting a basal rate profile.

To begin modifying one of the basal rate profiles 68 included in the configuration file 80, the operator activates an options button 170 associated with the respective basal rate profile. FIG. 7 depicts the result of activating options button 170 associated with profile one (for purposes of discussion, profile 70) depicted in FIG. 6. As shown, a pop-up basal profile dialog window 188 is displayed to the operator. Basal profile dialog window 188 includes a title bar 190 indicating the active profile 70, an instructions area 192 that provides information about modifying parameters of the active profile 70, a command bar 194, a maximum hourly basal rate text field 196 and associated up/down arrows 198, a profile graph 200, a group rate adjustment input area 202, a profile adjustment input area 204, a total dose indicator 206, an OK button 208 and a cancel button 210.

Profile graph 200 includes a plurality of graphical data representations 220 of the basal rates 222 for time periods 224 of the basal rate profile 70. Basal rates 222 correspond to the basal rate data values 74 of configuration file 80. Time periods 224 correspond to the time periods 72 of configuration file 80.

In the illustrated embodiment, the plurality of graphical data representations 220 are bar segments 230-276 of a bar graph and the time periods 224 are one hour blocks of a day. The bar segment for a respective time period fills the width of the time period which is represented on the x-axis of profile graph 200. The format of the x-axis may be set to a twelve hour clock format as shown in FIG. 7 or a twenty-four hour clock format as shown in FIG. 8.

A height of the bar segment for a respective time period corresponds to the basal rate for that time period. The basal rates are represented on the y-axis of profile graph 200. Value labels 226 are associated with each hourly basal rate 222. Value labels 226 provide a numerical value of the hourly basal rate of the respective bar segment 230-272. Although bar segments are used to represent the basal rates for a given time period other types of graphical representation may be implemented. Exemplary types of graphical representation include line graphs, point markers, sliders, and other types of graphical representation.

Figure 8:
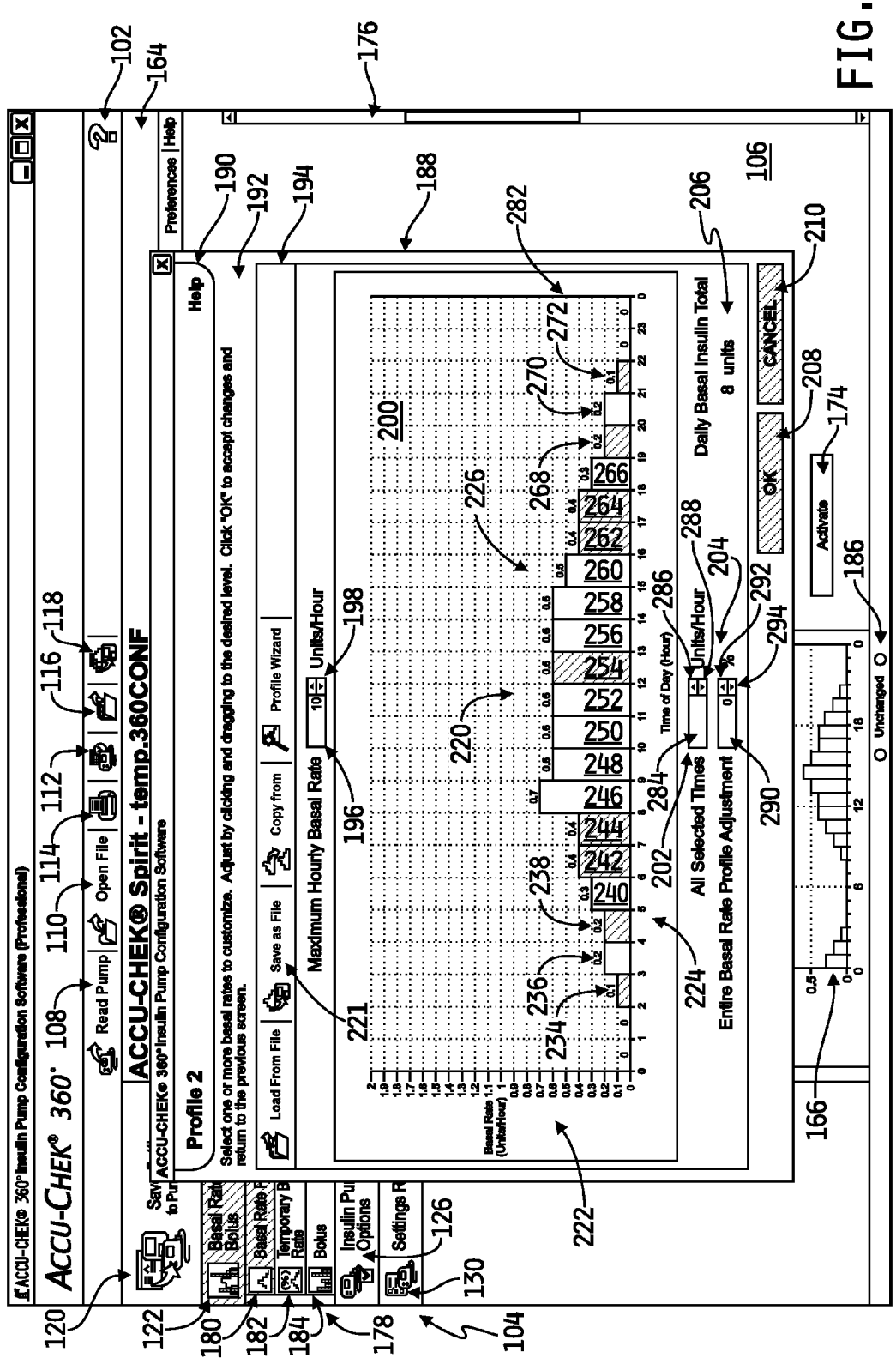
FIG. 8 is a screenshot of a profile edit window wherein a non-contiguous group of bar segments have been selected by the operator.

Referring to FIG. 8, the plurality of graphical data representations 220 for basal rates 222 are shown. It should be noted that FIG. 8 illustrates a different basal profile than FIG. 7. In FIG. 8, bar segments 230, 232, 274, and 276 are not shown because these time periods have a zero value basal rate 222 as indicated by the respective value labels 226.

Software 17 permits an operator to select user defined groups of bar segments 230-276. As explained herein, these user defined groups may be a contiguous group of bar segments or a non-contiguous group of bar segments. The operator may then alter the basal rates 222 represented by the group of bar segments. In one example, the basal rates 222 represented by the group of bar segments is changed by a constant offset amount. In another example, the basal rates 222 represented by the group of bar segments is changed by a percentage amount. In a further example, the basal rates 222 represented by the group of bar segments is changed to a constant value. The operator may also select a single bar segment and change the basal rate 222 represented by that bar segment.

FIG. 8 illustrates a method of selecting a first portion of the plurality of bar segments 230-276 to adjust the basal rates 222 associated with the first portion of the plurality of bar segments 230-276. In FIG. 8, bar segments 234, 238, 242, 244, 254, 262, 264, 268, and 270 have been selected as a first portion 280. First portion 280 is an exemplary non-contiguous group of bar segments in that bar segments 234, 238, 242, 244, 254, 262, 264, 268, and 270 do not correspond to successive time periods 224, but rather non-selected time periods exist between at least two of the bar segments 234, 238, 242, 244, 254, 262, 264, 268, and 270. For example, bar segment 236 between bar segments 234 and 238 is not a part of first portion 280.

In one embodiment, bar segments 234, 238, 242, 244, 254, 262, 264, 268, and 270 are selected by a series of inputs by an operator with input devices 16, 20. In one embodiment, an operator selects a first bar segment with pointer device 20, selects an input for a non-contiguous group with keyboard 16, and selects the remaining bar segments for first portion 280. In one example, a user selects bar segments 242 by placing a cursor visible on screen 18 over bar segments 242 and clicking a button on pointer device 20. The user then holds down the control key 21 on keyboard 16 to indicate a desire to select a non-contiguous group of bar segments. While holding down control key 21, the user selects the remaining bar segments 234, 238, 244, 254, 262, 264, 268, and 270 by placing the cursor visible on screen 18 over each of the remaining bar segments and clicking a button on pointer device 20. Once all of the desired bar segments have been selected, control key 21 may be released.

In one example, control key 21 may be released and reselected between the selections of the various bar segments. However, if control key 21 is not depressed at the time a given bar segment is selected then the previously selected bar segments will be removed from the group and a new group will be started with the given bar segment as the first selected bar segment. The members of first portion 280 are indicated by a visual indicator on screen 18. In one example, the visual indicator is that bar segments 234, 238, 242, 244, 254, 262, 264, 268, and 270 are a shown in a first color while the remaining bar segments are shown in a second color.

In one embodiment, the cursor may be anywhere within the column of graph 200 to select the bar segment within that column even if the cursor is outside of the area of the column containing the bar segment. This allows, among other things, for the selection of time periods currently having a zero value basal rate and thus no displayed bar segment. In another embodiment, the cursor must be within the bar segment to select the bar segment.

The combination of clicking an input of pointer device 20 and depressing control key 21 is one example of a method of selecting a non-contiguous group of bar segments, such as first portion 280. In one embodiment, a non-contiguous group button or other input is provided on basal profile dialog window 188 and is selected by a user who then selects the bar segments with pointer device 20. In another embodiment, screen 18 is a touch screen and the members of first portion 280 are selected by touching bar segments 234, 238, 242, 244, 254, 262, 264, 268, and 270.

Once first portion 280 is selected the basal rates 222 of the members of first portion 280 may be adjusted. As shown in FIG. 8, an outline 282 is provided. Outline 282 is static and provides an indication of the original basal rates 222 of all of the time periods 224 of the basal profile 70 read from either memory 15 or insulin pump 24.

Figure 9:
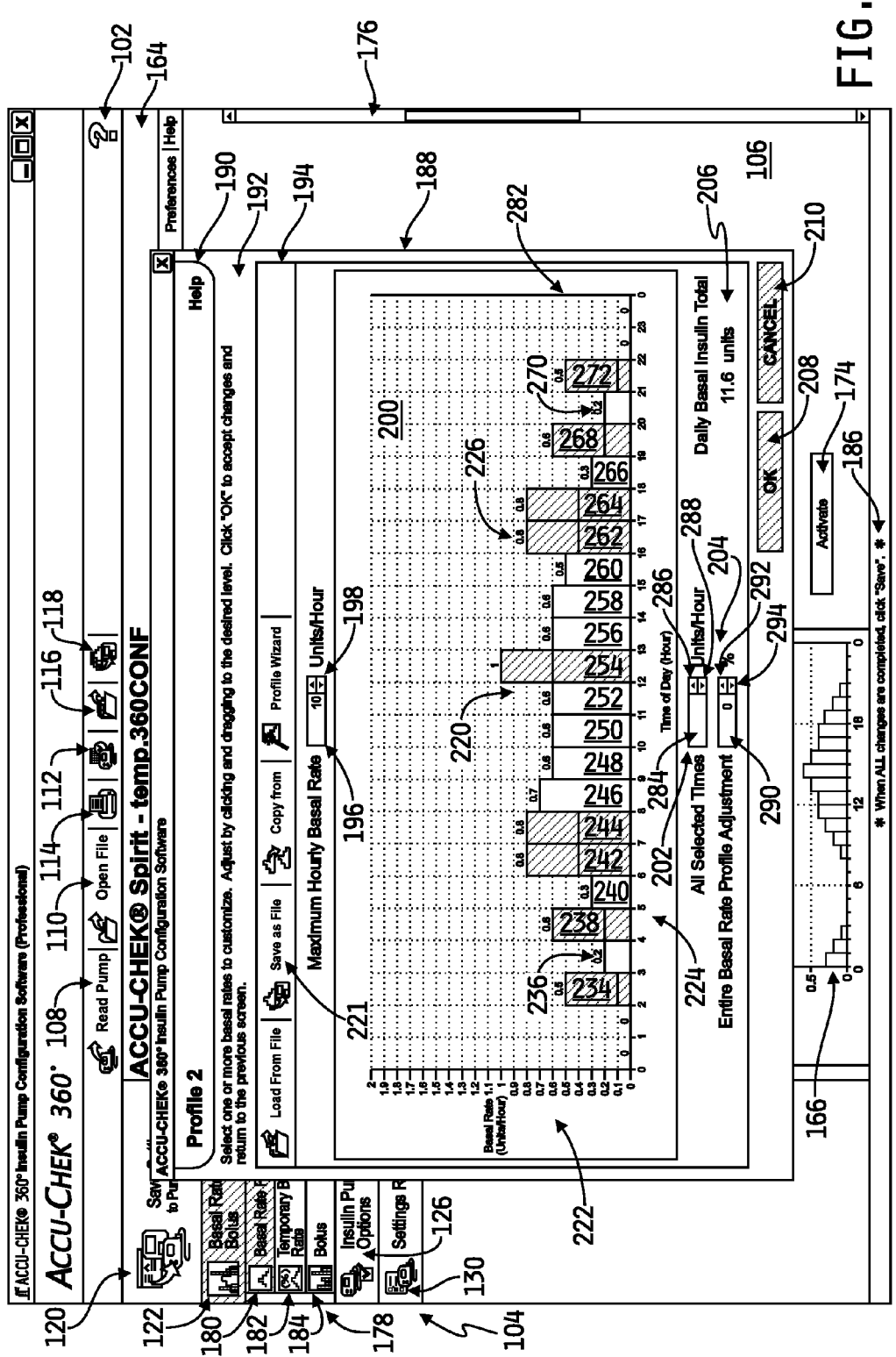
FIG. 9 is a screenshot of the profile edit window of FIG. 8 wherein the non-contiguous group of bar segments have been adjusted by a constant offset.

The basal rates 222 for first portion 280 may be set to a constant rate. Referring to FIG. 9, group rate adjustment input area 202 provides an entry field 284 wherein an operator may provide a basal rate. In one embodiment, the operator provides the basal rate to entry field 284 through use of numeric keys on keyboard 16. The operator may specify any desired basal rate in entry field 284. Of course, software 17 includes safety precautions to ensure that the specified insulin levels are safe for the user of insulin pump 24. Additional details regarding these safety precautions are disclosed in the Invalid Settings Application incorporated above.

The basal rates 222 for first portion 280 may be set to a constant rate through spinner controls, up arrow 286 and down arrow 288. Up arrow 286 increases the basal rate 222 by a set increment each time up arrow 286 is clicked. Down arrow 288 decreases the basal rate 222 by a set increment each time down arrow 288 is clicked. In one example, the basal rate cannot be set to a negative value.

Figure 10:
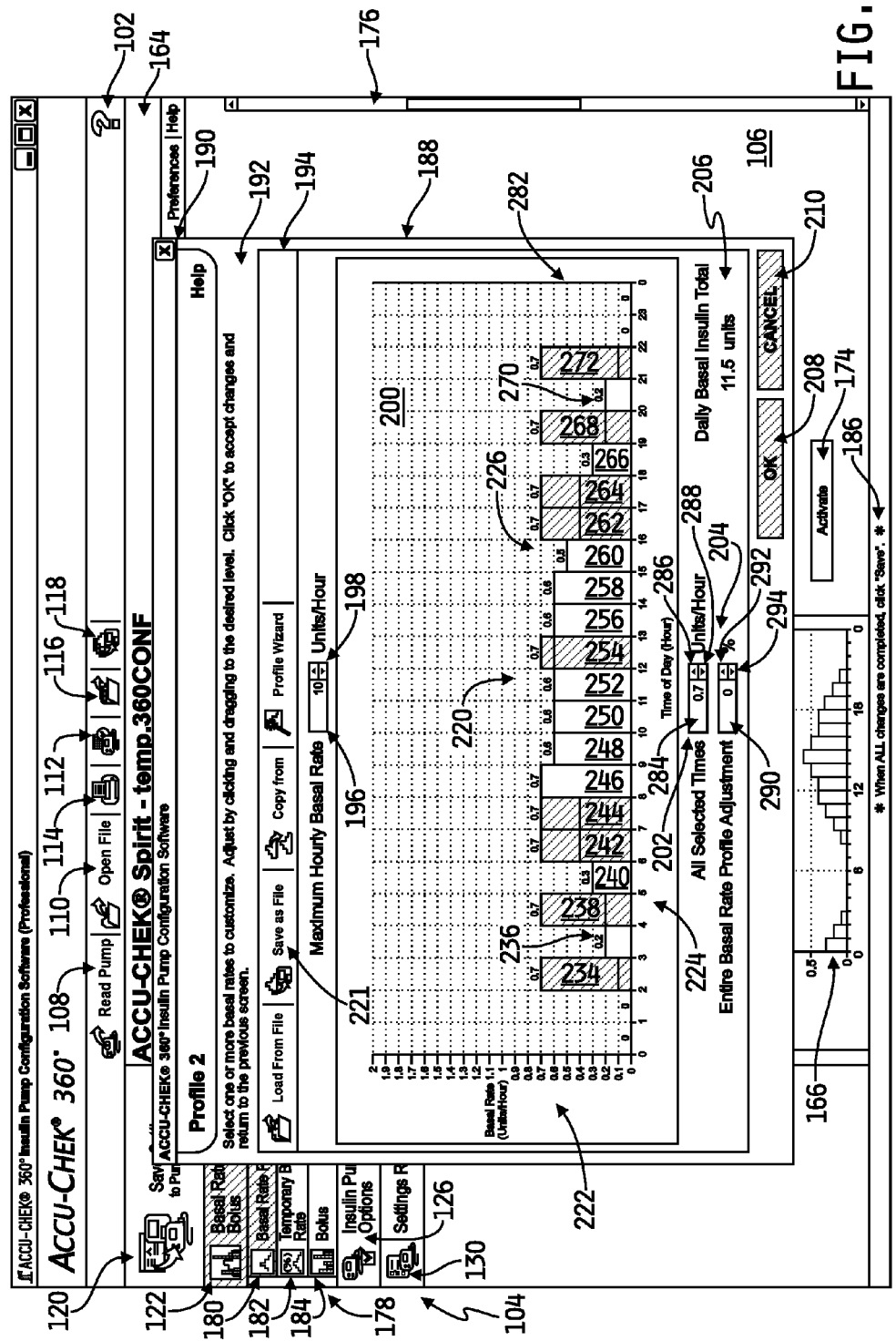
FIG. 10 is a screenshot of the profile edit window of FIG. 8 wherein the non-contiguous group of bar segments have been adjusted to a constant value.

Regardless of the method used to select a constant basal rate, bar segments 234, 238, 242, 244, 254, 262, 264, 268, and 270 are adjusted to reflect the entered constant basal rate. As shown in FIG. 10, the user has entered 0.7 in entry field 284 and each of bar segments 234, 238, 242, 244, 254, 262, 264, 268, and 270 has an adjusted basal rate of 0.7.

Alternatively, the basal rates 222 for first portion 280 may be offset by a constant offset. Referring to FIG. 9, each of bar segments 234, 238, 242, 244, 254, 262, 264, 268, and 270 has been increased by 0.4 units per hour.

In one embodiment, the operator provides the constant offset by selecting a top portion of one of the bar segments of first portion 280 with pointer device 20 and dragging the top portion to the desired basal rate. Once at the desired offset, the operator releases the top portion. Each of the remaining bar segments in the group are increased in height or decreased in height by the same offset simultaneously.

In one example, the operator selects the top portion by depressing a button on pointer device 20 and releases the top portion by releasing the button on pointer device 20. In one example, the cursor associated with pointer device 20 on screen 18 changes to indicate that a top portion of a selected bar segment may be dragged. In one case, the cursor is a hand icon or single headed arrow until it is positioned over a top portion of a selected bar segment. At that point, the cursor changes to a double-headed arrow to indicate that the top portion of the bar segment may be offset in a first direction to reduce the height or magnitude of the bar segments of first portion 280 or a second direction to increase the height or magnitude of the bar segments of first portion 280.

In another embodiment, operator provides the constant offset through one or a series of inputs with keyboard 16. In one example, the height or magnitude of the bar segments of first portion 280 are increased by selecting a first key of keyboard 16. To further increase the height or magnitude of the bar segments of first portion 280 the first key is selected again. The height or magnitude of the bar segments of first portion 280 may be decreased by selecting a second key of keyboard 16. To further decrease the height or magnitude of the bar segments of first portion 280 the second key is selected again. In one case, the first key is an up arrow 25 and the second key is a down arrow 27 (FIG. 1).

In a further embodiment, basal profile dialog window 188 includes at least one of an entry field and spinner controls by which an operator may specify a constant offset for the bar segments of first portion 280.

Figure 11:
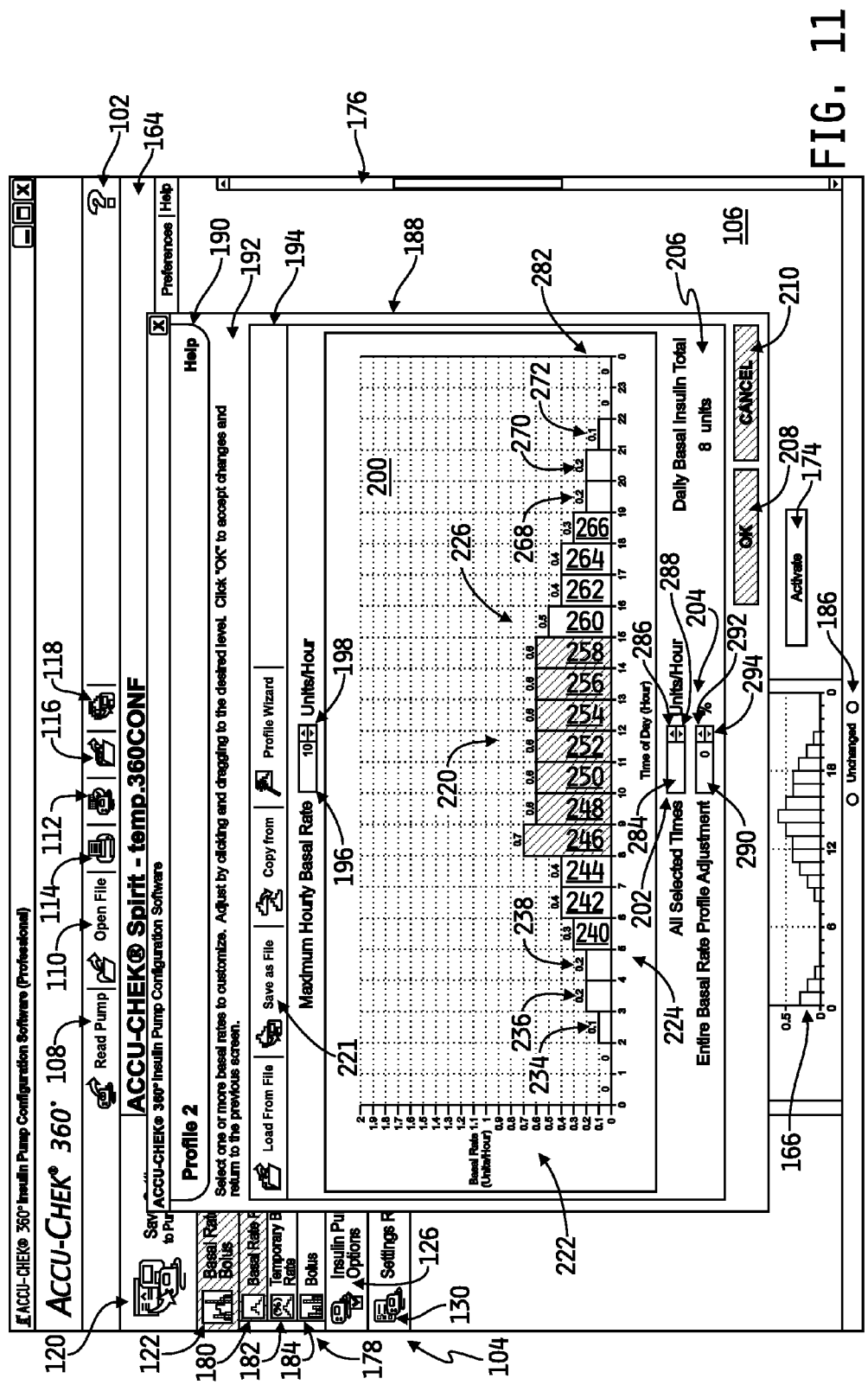
FIG. 11 is a screenshot of a profile edit window wherein a contiguous group of bar segments have been selected by the operator.

FIG. 11 illustrates a method of selecting a second portion 300 of the plurality of bar segments 230-276 to adjust the basal rates 222 associated with the second portion 300 of the plurality of bar segments 230-276. In FIG. 11, bar segments 246-258 have been selected as second portion 300. Second portion 300 is an exemplary contiguous group of bar segments in that bar segments 246-258 correspond to successive time periods 224.

In one embodiment, bar segments 246-258 are selected by a series of inputs by an operator with input devices 16, 20. In one embodiment, an operator selects a first bar segment with pointer device 20, selects an input for a contiguous group with keyboard 16, and selects the remaining bar segments for second portion 300. In one example, a user selects bar segments 246-258 by placing a cursor visible on screen 18 over bar segments 246 and clicking a button on pointer device 20. The user then holds down the shift key 23 on keyboard 16 to indicate a desire to select a contiguous group of bar segments. While holding down shift key 23, the user selects the remaining bar segments 248-258 by placing the cursor visible on screen 18 over bar segment 258 and clicking a button on pointer device 20. Software 17 interprets this sequence of inputs as an indication to select bar segment 246, bar segment 258, and all bar segments in between. Once all of the desired bar segments have been selected, shift key 23 may be released. In one example, shift key 23 may be released and reselected between the selection of a first bar segment and a second bar segment. However, if shift key 23 is not depressed at the time a given bar segment is selected then the previously selected bar segment will be removed from the group and a new group will be started with the given bar segment as the first selected bar segment. The members of second portion 300 are indicated by a visual indicator on screen 18. In one example, the visual indicator is that bar segments 246-258 are shown in a first color while the remaining bar segments are shown in a second color.

In one embodiment, wherein second portion 300 includes the first bar segment 230, second portion 300 may be selected with two inputs. In one example, the user holds down the shift key 23 on keyboard 16 to indicate a desire to select a contiguous group of bar segments and then selects a bar segment other than bar segment 230 by placing a cursor visible on screen 18 over the bar segment and clicking a button on pointer device 20. This results in all bar segment between and inclusive of bar segment 230 and the selected bar segment being in second portion 300.

The combination of clicking an input of pointer device 20 and depressing shift key 23 is one example of a method of selecting a contiguous group of bar segments, such as second portion 300. In one embodiment, a contiguous group button or other input is provided on basal profile dialog window 188 and is selected by a user who them selects the two end bar segments of the group. In another embodiment, screen 18 is a touch screen and the members of first portion 280 are selected by touching bar segments 246-258.

Figure 12:
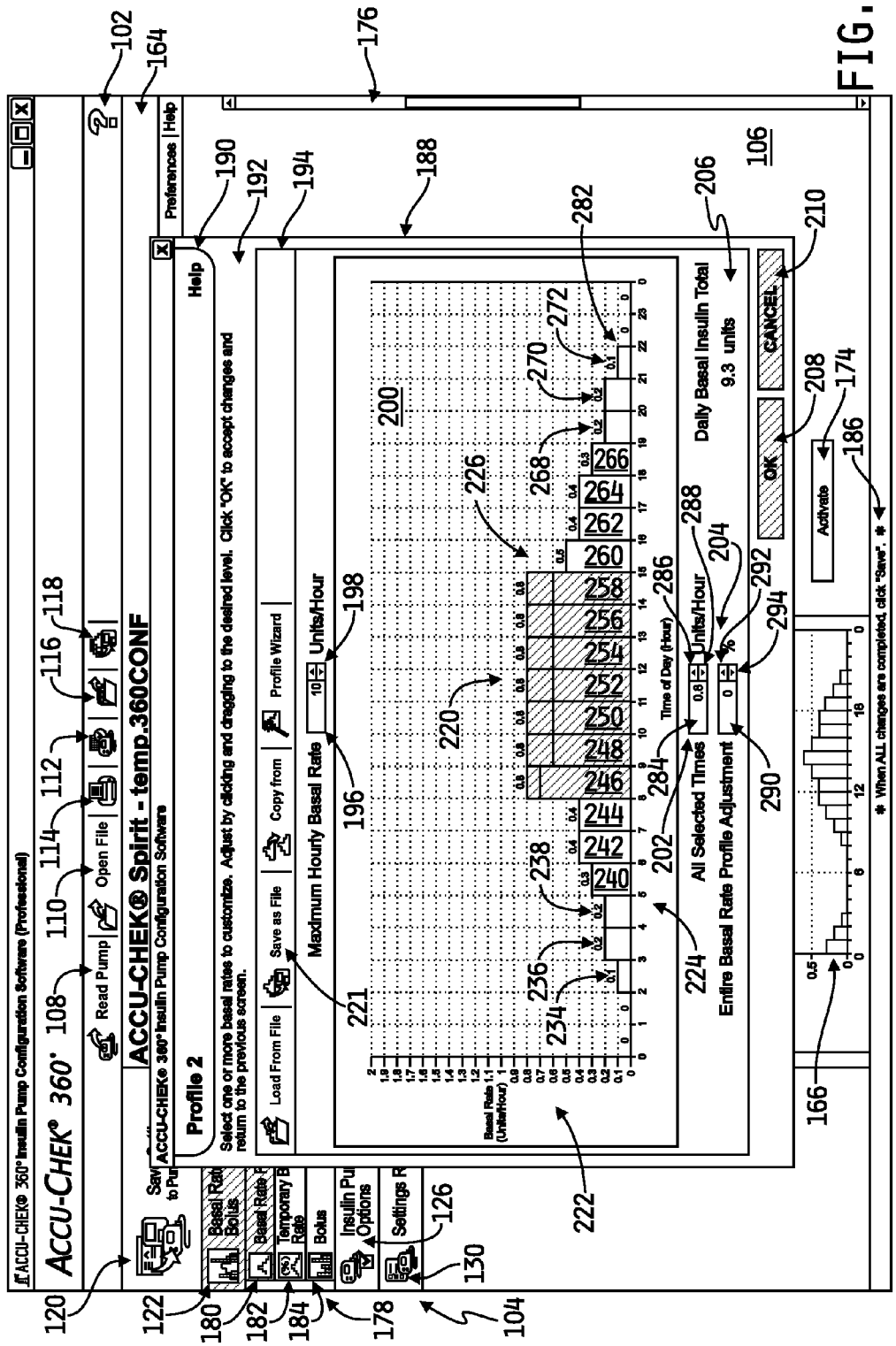
FIG. 12 is a screenshot of the profile edit window of FIG. 11 wherein the non-contiguous group of bar segments have been adjusted to a constant value.

Once second portion 300 is selected the basal rates 222 of the members of second portion 300 may be adjusted. As shown in FIG. 12, outline 282 is also provided for contiguous groups. The basal rates 222 of second portion 300 may be changed through use of numeric keys on keyboard 16. The operator may specify any desired basal rate in entry field 284 as described herein for non-contiguous groups. The basal rates 222 of second portion 300 may be set to a constant rate through spinner controls, up arrow 286 and down arrow 288 as described herein for non-contiguous groups.

Regardless of the method used to select a constant basal rate, bar segments 246-258 are adjusted to reflect the entered constant basal rate. As shown in FIG. 12, the user has entered 0.8 in entry field 284 and each of bar segments 246-258 have adjusted basal rates of 0.8.

Figure 13:
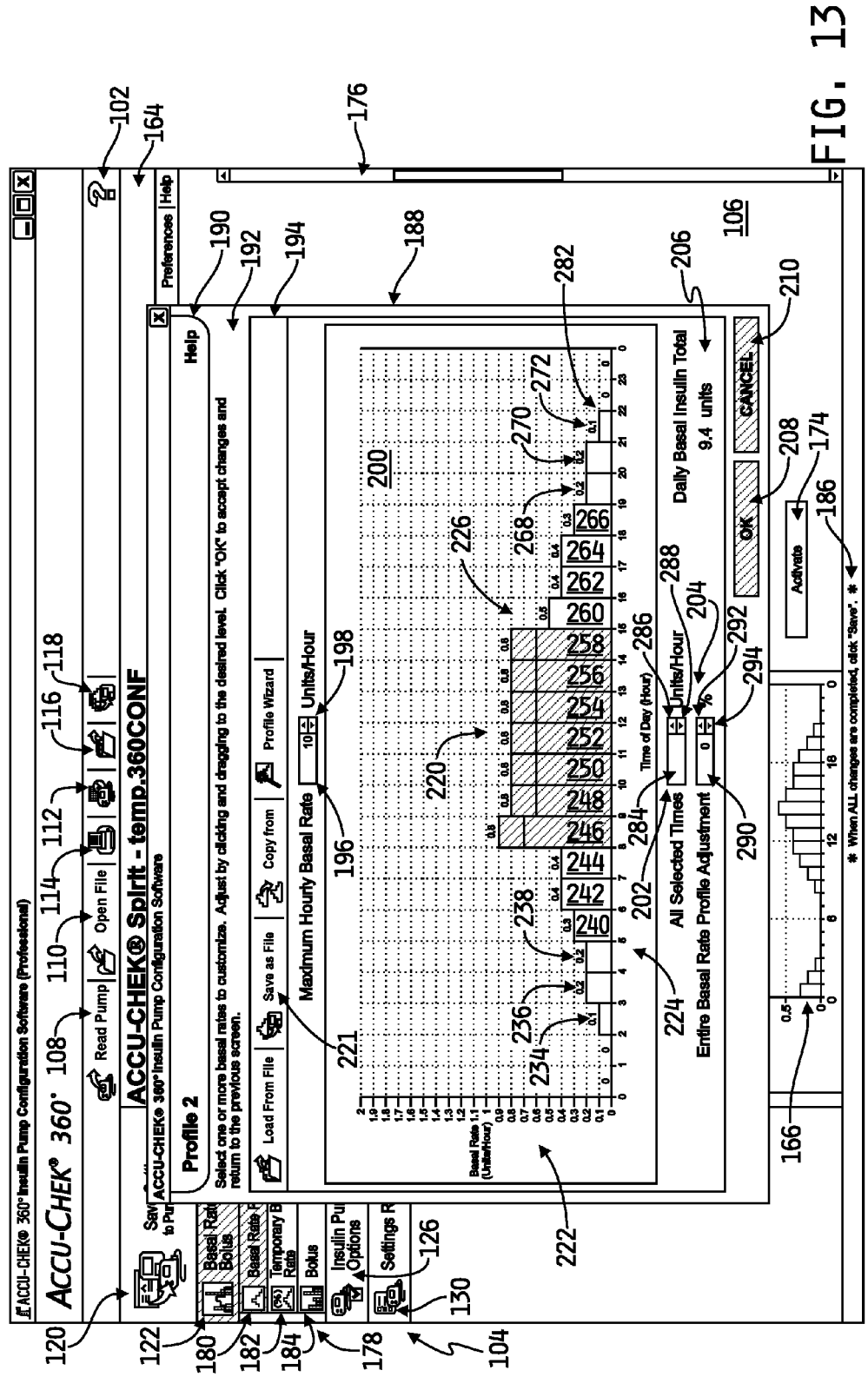
FIG. 13 is a screenshot of the profile edit window of FIG. 11 wherein the non-contiguous group of bar segments have been adjusted by a constant offset.

The basal rates 222 of second portion 300 may be offset by a constant offset. Referring to FIG. 13, each of bar segments 246-258 has been increased by 0.2 units per hour.

In one embodiment, the operator provides the constant offset by selecting a top portion of one of the bar segments of second portion 300 with pointer device 20 and dragging the top portion to the desired basal rate as described herein for non-contiguous groups. Once at the desired offset, the operator releases the top portion. Each of the remaining bar segments are increased in height or decreased in height by the same offset simultaneously.

In another embodiment, operator provides the constant offset through one or a series of inputs with keyboard 16 as described herein for non-contiguous groups.

In a further embodiment, basal profile dialog window 188 includes at least one of an entry field and spinner controls by which an operator may specify a constant offset for the bar segments of second portion 300.

The operator may adjust all of the basal rates by a percentage amount with profile adjustment input area 204. Profile adjustment input area 204 provides an entry field 290 wherein an operator may provide a percentage adjustment to the entire profile of basal rates. In one embodiment, the operator provides the percentage adjustment to entry field 284 through use of numeric keys on keyboard 16. The operator may specify any desired basal rate in entry field 284. Of course, software 17 includes safety precautions to ensure that the specified insulin levels are safe for the user of insulin pump 24. Additional details regarding these safety precautions are disclosed in the Invalid Settings Application incorporated above The percentage adjustment to the entire profile of basal rates may be set to a constant rate through spinner controls, up arrow 292 and down arrow 294. Up arrow 292 increases the basal rate 222 by a set percentage adjustment each time up arrow 292 is clicked. Down arrow 294 decreases the basal rate 222 by a set percentage adjustment each time down arrow 294 is clicked.

As is well understood in the art, pump 24 delivers insulin to the user substantially continuously. Various physiological factors influence the appropriate amount of insulin to deliver to the user, and the appropriate delivery rate fluctuates throughout the day. By manipulating profile graph 200 and/or using other controls provided on basal profile dialog window 188, the operator may make changes to any of hourly basal rates 212. The techniques facilitated for making such adjustments, and the operation of group rate adjustment area 202 and profile adjustment area 204 are described herein. By providing all twenty-four time periods in profile graph 200, an operator is able to select the basal rates for all time periods at the same time or select subgroups of time periods across the spectrum from the first hour of the day to the last hour of the day.

Regardless of whether the operator has made one adjustment or multiple adjustments to basal rate profile 70, the operator may save the adjusted data values for the basal rates configuration file 80 to a memory 15 associated with computing device 12 by activating save as file button 221. In one embodiment, the operator is not permitted to save the configuration file to insulin pump 24 if there is an invalidity condition as disclosed in the Invalid Settings Application.

While an exemplary embodiment incorporating the principles of the present teachings has been disclosed hereinabove, the present teachings are not limited to the disclosed embodiments. Instead, this application is intended to cover any variations, uses, or adaptations of the disclosed general principles. For instance, instead of adjusting the basal rates of a basal rate profile the adjustment techniques used herein may be employed to provide an adjustment of the data values of a profile through graphical representations of the profile. Further, this application is intended to cover such departures from the present disclosure as come within known or customary practice in the art to which this application pertains and which fall within the limits of the appended claims.

What is claimed is:

1. A method for adjusting data values via a medical apparatus programming device, including the steps of:
displaying a plurality of data representations in a graphical format on a display of the medical apparatus programming device, each data representation corresponding to a data value of a profile;
receiving a selection of a first portion of the plurality of data representations, the first portion of the plurality of data representations including a non-contiguous group of the plurality of data representations;
receiving at least one input to simultaneously adjust the data representations of the non-contiguous group of data representations without adjusting data representations not part of the non-contiguous group of data representations; and
adjusting the data values of the profile corresponding to the data representations of the non-contiguous group of data representations based on the received at least one input without adjusting data representations not part of the non-contiguous group of data representations.

2. The method of claim 1, wherein the step of receiving the at least one input to simultaneously adjust the data representations of the non-contiguous group of data representations includes the step of altering the plurality of data representations of the first portion to represent one of a reduction in the corresponding data values of the profile by a first offset and an increase in the corresponding data values of the profile by a second offset.

3. The method of claim 2, wherein the plurality of data representations are bar segments of a bar graph and the step of altering the plurality of data representations of the non-contiguous group to represent one of a reduction in the corresponding data values of the profile by a first offset and an increase in the corresponding data values of the profile by a second offset includes the step of with a pointer device simultaneously dragging a current height of each the bar segments of the first portion to an adjusted height corresponding to one of the first offset from the current height and the second offset from the current height.

4. The method of claim 2, wherein the plurality of data representations are bar segments of a bar graph and the step of altering the plurality of data representations of the non-contiguous group to represent one of a reduction in the corresponding data values of the profile by a first offset and an increase in the corresponding data values of the profile by a second offset includes the step of with a keyboard simultaneously moving a current height of each the bar segments of the first portion to an adjusted height corresponding to one of the first offset from the current height and the second offset from the current height, a first key of the keyboard being used to move the current height of each of the bar segments of the non-contiguous group to the adjusted height corresponding to the first offset and a second key of the keyboard being used to move the current height of each of the bar segments of the non-contiguous group to the adjusted height corresponding to the second offset.

5. The method of claim 1, wherein the step of receiving at least one input includes receiving at least one input to simultaneously adjust the data representations of the non-contiguous group of data representations without adjusting data representations not part of the non-contiguous group of data representations; and the step of adjusting the data values includes adjusting the data values of the profile corresponding to the data representations of the non-contiguous group of data representations based on the received at least one input without adjusting data representations not part of the non-contiguous group of data representations.

6. A method of adjusting insulin basal rates for an insulin pump, the method including the steps of:
receiving a plurality of insulin basal profiles from the insulin pump by a medical device, each of the plurality of insulin basal profiles providing insulin basal rates for a plurality of time periods of a twenty-four hour period;
storing the plurality of insulin basal profiles;
displaying a first graphical representation of each of the plurality of insulin basal profiles;
receiving a selection of a first insulin basal profile of the plurality of insulin basal profiles,
displaying a second graphical representation of the first insulin basal profile, the second graphical representation including a first axis indicating a time scale, a second axis indicating an insulin basal rate scale, and a plurality of data representations each data representation corresponding to a time period of the plurality of time periods and providing an indication of a corresponding insulin basal rate for the time period;
receiving a selection of a first non-contiguous grouping of data representations corresponding to a first non-contiguous grouping of time periods of the first insulin basal rate profile;
simultaneously adjusting the first non-contiguous grouping of data representations to adjust an indication of the corresponding insulin basal rate for each of the time periods of the first non-contiguous grouping of time periods without adjusting data representations not part of the non-contiguous group of data representations;
storing an adjusted first insulin basal rate profile, the adjusted first insulin basal rate profile including adjusted insulin basal rates for the first non-contiguous grouping of time periods, the adjusted insulin basal rates being based on the adjusted first non-contiguous grouping of data representations; and
communicating the adjusted first insulin basal rate profile to the insulin pump.

7. The method of 6, wherein the plurality of data representations are bar segments and the indication of the corresponding insulin basal rate for each of the plurality of data representations includes a height of the corresponding bar segment.

8. The method of 7, wherein the step of receiving the selection of the first non-contiguous grouping of data representations corresponding to the first non-contiguous grouping of time periods of the first insulin basal rate profile includes the steps of:
receiving a first input selecting a first bar segment of the bar segments of the first non-contiguous grouping of data representations; and
receiving a second input selecting a second bar segment of the bar segments of the first non-contiguous grouping of data representations; and
wherein the step of simultaneously adjusting the first non-contiguous grouping of time periods includes the steps of:
receiving a third input corresponding to adjusting a height of the first non-contiguous grouping of data representations including a first adjusted height corresponding to the first bar segment and a second adjusted height corresponding to the second bar segment; and
displaying the plurality of bar segments corresponding to the first non-contiguous grouping of data representations, the first bar segment being displayed with the first adjusted height and the second bar segment being displayed with the second adjusted height.

9. The method of claim 8, wherein the step of receiving the selection of the first non-contiguous grouping of data representations corresponding to the first non-contiguous grouping of time periods of the first insulin basal rate profile further includes the step of receiving a fourth input selecting a group type as a non-contiguous group, the fourth input being received prior to the second input.

10. The method of claim 8, wherein the third input corresponds to a fixed offset.

11. The method of claim 8, wherein the third input corresponds to a percentage offset.

12. The method of claim 8, further including the step of displaying a representation of an original first height of the first bar segment along with the first adjusted height of the first bar segment and an original second height of the second bar segment along with the second adjusted height of the second bar segment.

13. A method for adjusting data values, including the steps of:
displaying a plurality of data representations in a graphical format on a display of a medical apparatus programming device, each data representation corresponding to a data value of a profile;
receiving a first input corresponding to a selection of a first data representation and a second input, the second input corresponding to one of a contiguous group selection and a non-contiguous group selection;
receiving a third input corresponding to a selection of a second data representation;
defining a contiguous group of data values of the profile corresponding to data representations bounded by the first data representation and the second data representation when the second input corresponds to the contiguous group selection;
defining a non-contiguous group of data values of the profile corresponding to data representations including the first data representation and the second data representation when the second input corresponds to the non-contiguous group selection; and
simultaneously adjusting each of the defined group of data values in response to a received adjustment input without adjusting data representations not part of the defined group of data values.

14. The method of claim 13, wherein the profile is a basal rate profile for an insulin pump and the plurality of data values are a plurality of basal rates of insulin to be administered by the insulin pump.

15. The method of claim 14, wherein the plurality of data representations are a plurality of bar segments corresponding to the plurality of basal rates of insulin to be administered by the insulin pump.

16. The method of claim 14, further including the steps of:
   storing an adjusted basal rate profile including each of the data values of the defined group; and
   communicating the adjusted basal rate profile to the insulin pump.

17. The method of claim 13, wherein the first input and the third input is received from a pointing device and the second input is received from a keyboard.

18. The method of claim 17, wherein the second input corresponding to a contiguous group selection is based on a shift key of the keyboard and the second input corresponding to a non-contiguous group selection is based on a control key of the keyboard.

19. The method of claim 13, wherein the simultaneously adjusting step includes the step of receiving inputs from a pointing device resulting from a user clicking on a data representation corresponding to one of the data values in the defined group of data values and altering a position of the data representation.

20. The method of claim 19, wherein the simultaneously adjusting step includes the step of changing each of the data values in the defined group by an offset, the offset corresponding to the position of the data representation.

21. The method of claim 13, wherein the simultaneously adjusting step includes the steps of setting each of the data values in the defined group to an equal value and changing each of the data values in the defined group by a fixed amount.

22. The method of claim 13, further including the step of displaying adjusted data representations corresponding to the defined group as a real time visual feedback.

23. The method of claim 13, further including the step of displaying an adjustment field, wherein the simultaneously adjusting step includes the step of receiving an input from a keyboard resulting from a user entering a value in the adjustment field.

24. The method of claim 23, wherein the simultaneously adjusting step includes the step of setting each of the data values in the defined group to the entered value.

25. An apparatus for adjusting insulin basal rates for an insulin pump, the apparatus comprising:
   a computing device;
   a memory accessible by the computing device;
   a display operatively coupled to the computing device;
   at least one user input device operatively coupled to the computing device; and
   software stored on the memory which provides a user interface to display a graphical representation of a first insulin basal profile for the insulin pump including a data representation for a plurality of time periods of the first insulin basal profile and corresponding insulin basal rates for each of the plurality of time periods, the software including means for selecting a non-contiguous group of data representations of a first portion of the plurality of time periods for adjustment and means for simultaneously adjusting the corresponding insulin basal rates for each of the data representations of the first portion of the plurality of time periods without adjusting data representations not part of the first portion of the plurality of time periods.

26. The apparatus of claim 25, wherein the software further includes means for selecting a contiguous group of data representations of a second portion of the plurality of time periods for adjustment.

27. The apparatus of claim 25, wherein the means for simultaneously adjusting the corresponding insulin basal rates for each of the data representations of the first portion of the plurality of time periods includes means for adjusting the corresponding basal rates for each of the data representations of the first portion of the plurality of time periods by a fixed offset.

28. The apparatus of claim 25, wherein the means for simultaneously adjusting the corresponding insulin basal rates for each of the data representations of the first portion of the plurality of time periods includes means for adjusting the corresponding basal rates for each of the data representations of the first portion of the plurality of time periods by a percentage.

29. A computer readable medium tangibly embodying instructions executable by a computing device to perform method steps including:
   displaying a graphical representation of a current basal rate profile, the basal rate profile having a plurality of time periods and associated basal rates and the graphical representation including a plurality of data representations corresponding to the plurality of time periods and associated basal rates of the basal rate profile;
   permitting the selection of a non-contiguous group of the plurality of data representations; and
   simultaneously adjusting a characteristic of the non-contiguous group of the plurality of data representations, without adjusting the characteristic not part of the non-contiguous group, to represent an adjusted basal rate for each of the time periods of the non-contiguous group of the plurality of data representations.

30. The computer readable medium of claim 29, further including instructions to display the current basal rate profile and the adjusted basal rate profile simultaneously.

* * * * *